US012714340B2

(12) United States Patent
Huang et al.

(10) Patent No.: US 12,714,340 B2
(45) Date of Patent: Aug. 25, 2026

(54) SIDELIGHT TYPE NON-INVASIVE GLUCOSE MONITORING MODULE

(71) Applicant: Taiwan-Asia Semiconductor Corporation, Hsinchu City (TW)

(72) Inventors: Hsiu-Jung Huang, Hsinchu City (TW); Sheng-Wei Chen, Hsinchu City (TW)

(73) Assignee: TAIWAN-ASIA SEMICONDUCTOR CORPORATION, Hsinchu City (TW)

( * ) Notice: Subject to any disclaimer, the term of this patent is extended or adjusted under 35 U.S.C. 154(b) by 320 days.

(21) Appl. No.: 18/536,609

(22) Filed: Dec. 12, 2023

(65) Prior Publication Data

US 2024/0188858 A1 Jun. 13, 2024

(30) Foreign Application Priority Data

Dec. 13, 2022 (TW) ................................ 111147880

(51) Int. Cl.
*A61B 5/1455* (2006.01)
*A61B 5/145* (2006.01)

(52) U.S. Cl.
CPC ........ *A61B 5/1455* (2013.01); *A61B 5/14532* (2013.01); *A61B 2562/0233* (2013.01); *A61B 2562/185* (2013.01)

(58) Field of Classification Search
CPC ............. A61B 5/1455; A61B 5/14551; A61B 5/14552; A61B 5/14532; A61B 2562/0233; A61B 2562/185
See application file for complete search history.

(56) References Cited

U.S. PATENT DOCUMENTS

| | | | | |
|---|---|---|---|---|
| 7,643,860 | B2 * | 1/2010 | Gueissaz | A61B 5/681 600/310 |
| 10,105,081 | B2 * | 10/2018 | Delbeke | A61B 5/1455 |
| 10,722,157 | B2 * | 7/2020 | Bower | A61B 5/14552 |
| 2012/0188616 | A1 | 7/2012 | Takeda et al. | |
| 2020/0163601 | A1 * | 5/2020 | Rayer | A61B 5/14552 |

FOREIGN PATENT DOCUMENTS

TW 201536255 A 10/2015

OTHER PUBLICATIONS

Office Action (with Search Report) issued in corresponding TW application No. 111147880 dated Jan. 12, 2024 (5 pages).

* cited by examiner

*Primary Examiner* — Eric F Winakur
(74) *Attorney, Agent, or Firm* — MUNCY, GEISSLER, OLDS & LOWE, P.C.

(57) ABSTRACT

The invention provides a sidelight-type non-invasive glucose monitoring module, which includes a substrate, an sidelight-type light source assembly, an sidelight-type light sensing assembly and a blocking member. The sidelight-type light source assembly is arranged on the substrate and includes a light-emitting element and a first light-guiding element. The sidelight-type light sensing assembly is arranged on the substrate and includes a light-sensing element and a second light-guiding element. The blocking member is arranged between the sidelight-type light source assembly and the sidelight-type light sensing assembly to block the sidelight-type light source assembly from the sidelight-type light sensing assembly.

6 Claims, 2 Drawing Sheets

SIDELIGHT TYPE NON-INVASIVE GLUCOSE MONITORING MODULE

CROSS REFERENCE TO RELATED APPLICATION

This application claims the benefit of Taiwan Patent Application Serial No. 111147880 filed on Dec. 13, 2022. The entirety of each Application is incorporated herein by reference.

BACKGROUND OF THE INVENTION

1. Field of the Invention

The present invention relates to a glucose monitoring module. More particularly, the present invention relates to a non-invasive glucose monitoring module utilizing sidelight-type optical components.

2. Description of Related Art

General blood glucose sensing modules available on the market may typically be categorized into invasive and non-invasive types of sensing modules. As shown in FIG. 1, the conventional non-invasive blood glucose sensing module, denoted as "A", utilizes a light-emitting unit comprised of multiple LED elements A1 and a light-sensing unit comprised of multiple light-sensing elements A2 to detect blood glucose. When the area for blood glucose detection increases, both the number of LED elements A1 and the number of light-sensing elements A2 will inevitably increase, leading to higher manufacturing costs. Furthermore, because the light-emitting units and light-sensing units are arranged in a direct-illuminating-receiving approach, the conventional non-invasive blood glucose sensing module A has a certain thickness, making it difficult to reduce its thickness. Consequently, the conventional non-invasive blood glucose sensing modules face various limitations in structural design.

Hence, it is indeed crucial to address the issues mentioned above by designing a non-invasive blood glucose sensing device that can reduce its thickness, and lower manufacturing costs.

SUMMARY OF THE INVENTION

One object of the present invention is to provide a non-invasive glucose sensing module which utilizes sidelight-type optic components.

To achieve the object described above, the sidelight-type non-invasive glucose monitoring module includes a substrate, a sidelight-type light source assembly, a sidelight-type light sensing assembly and a blocking member. The sidelight-type light source assembly is disposed on the substrate and includes a light-emitting element and a first light-guiding element. The sidelight-type light sensing assembly is disposed on the substrate and includes a light-sensing element and a second light-guiding element. The blocking member is disposed between the sidelight-type light source assembly and the sidelight-type light sensing assembly. The blocking member is disposed to block the sidelight-type light source assembly from the sidelight-type light sensing assembly.

In one embodiment of the present invention, the blocking member is connected to the first light-guiding element and the second light-guiding element.

In one embodiment of the present invention, the blocking member is made from an opaque material.

In one embodiment of the present invention, the substrate comprises a bottom portion, a first side-portion and a second side-portion, the first side-portion being opposite to the second side-portion. The light-emitting element is disposed on the first side-portion, and the light-sensing element is disposed on the second side-portion.

In one embodiment of the present invention, the sidelight-type non-invasive glucose monitoring module further includes a reflective element disposed on the substrate and between the bottom portion and each of the first light-guiding element and the second light-guiding element. The reflective element is configured to reflect a light transmitted from the light-emitting element, or to reflect a light to the light-sensing element.

In one embodiment of the present invention, the sidelight-type light source assembly further includes a first dot portion formed on a surface, facing the bottom portion, of the first light-guiding element.

In one embodiment of the present invention, the sidelight-type light source assembly further includes a light-emitting coating formed on a surface, opposite to the bottom portion, of the first light-guiding element.

In one embodiment of the present invention, the second light-guiding element includes a second dot portion formed on a surface, facing the bottom portion, of the second light-guiding element.

In one embodiment of the present invention, the second light-guiding element includes an light-receiving coating formed on a surface, opposite to the bottom portion, of the second light-guiding element.

In one embodiment of the present invention, an opaque sealing member is disposed to connect with a junction of the sidelight-type light source assembly and the substrate and a junction of the sidelight-type light sensing assembly and the substrate.

Accordingly, the sidelight-type non-invasive glucose monitoring module of the present invention may effectively decrease the overall height of the device through the design of the sidelight-type optic component. Furthermore, only a single light-emitting element and a single light-sensing element are required to achieve the purpose of detecting glucose, thereby reducing the manufacturing coat.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION OF THE PREFERRED EMBODIMENT

The following disclosure provides many different embodiments, or examples, for implementing different features of the provided subject matter. Specific examples of components and arrangements are described below to simplify the present disclosure. These are, of course, merely examples and are not intended to be limiting.

In this disclosure, the term “one” or “a” is used to describe the elements, components and assemblies mentioned herein. This is done for the sake of convenience and to provide a general understanding of the scope of the present invention. Therefore, unless expressly stated otherwise, such descriptions should be understood to comprise one or at least one, and the singular form also comprise the plural.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the embodiments. As used herein, the term “and/or” includes any and all combinations of one or more of the associated listed items.

The terms “comprising,” “having,” or any similar terminology are intended to encompass non-exclusive inclusions. For example, a component or structure with multiple elements is not limited to only the elements listed in this document but may also include other elements that are inherently typical for that component or structure even if not explicitly listed.

In the present disclosure, the term “sidelight-type” means that light transmits in a lateral direction, i.e., a horizontal direction or a direction parallel to the bottom portion of the substrate. In other words, light primarily transmits from a light source in a lateral direction, or light is received primarily along a lateral direction.

Figure 1:
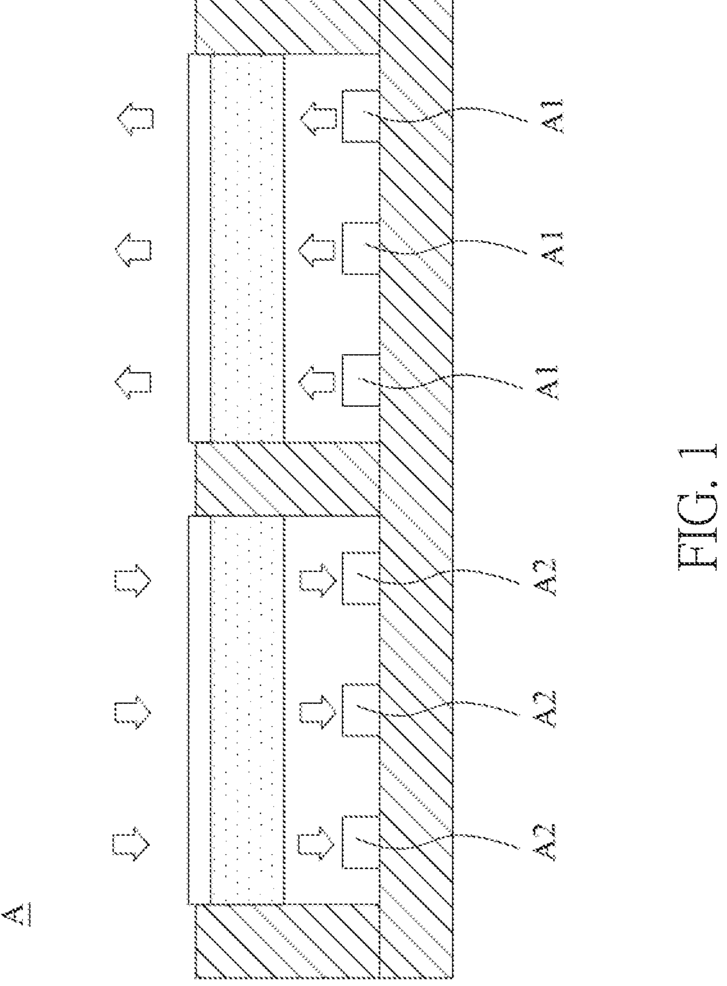
FIG. 1 is a cross-sectional view schematically illustrating a conventional non-invasive blood glucose sensing module.
Figure 2:
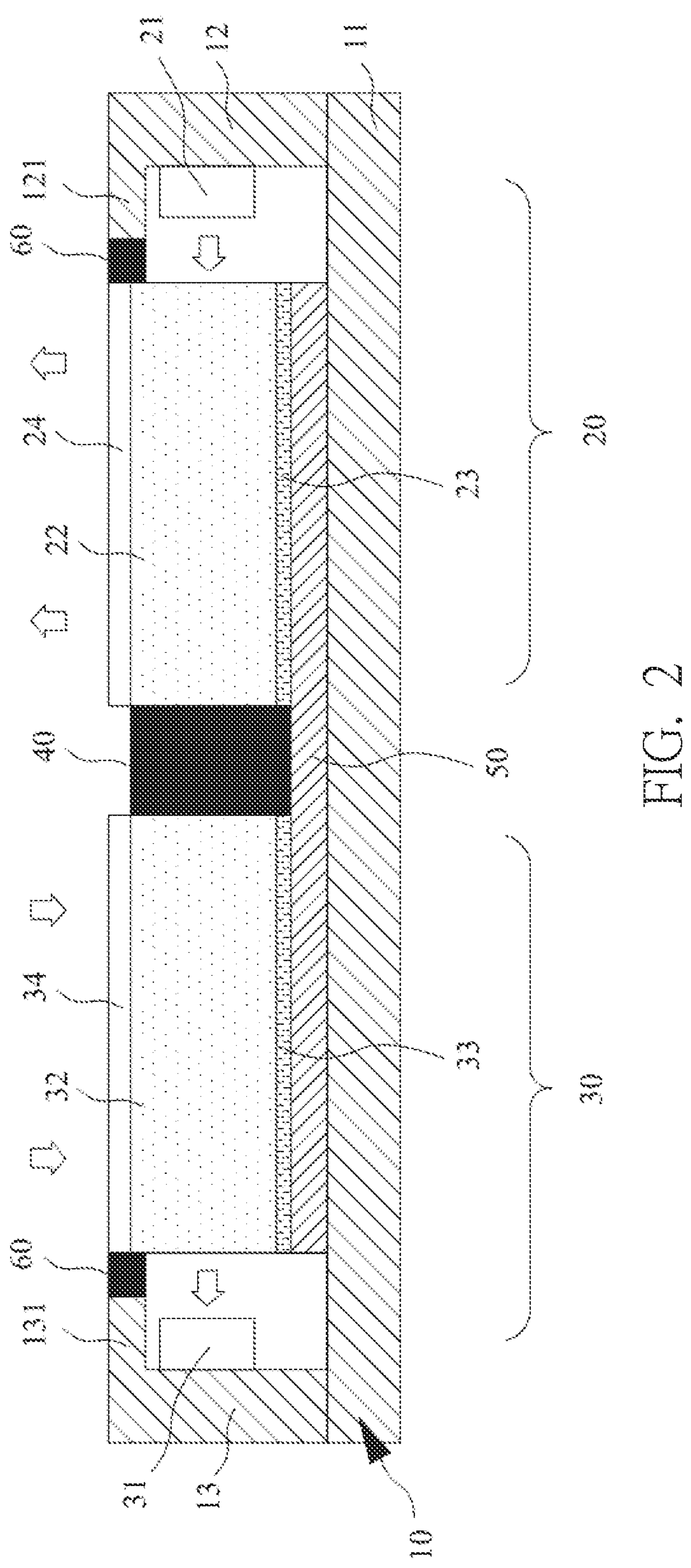
FIG. 2. is a cross-sectional view schematically illustrating a sidelight-type non-invasive glucose monitoring module according to some embodiments of the present invention.

FIG. 2 is a cross-sectional view schematically showing a sidelight-type non-invasive glucose monitoring module according to a first embodiment of the present invention. As shown in FIG. 2, the sidelight-type non-invasive glucose monitoring module 1, according to the present invention, includes a substrate 10, a sidelight-type light source assembly 20, a sidelight-type light sensing assembly 30 and a blocking member 40. The substrate 10 primarily serves as a base-structural component, and the substrate 10 may function to carry the sidelight-type light source assembly 20, the sidelight-type light sensing assembly 30 and the blocking member 40 so as to form an integral module.

In one embodiment of the present invention, the substrate 10 includes a bottom portion 11, a first side-portion 12 and a second side-portion 13, in which the first side-portion 12 is opposite to the second side-portion 13. The bottom portion 11 is substantially a plate in structure. One end of the first side-portion 12 is connected to an edge on one side of the bottom portion 11, and the first side-portion 12 is perpendicular to the bottom portion 11. Furthermore, one end of the second side-portion 13 is connected to an edge on another side of the bottom portion 11 opposite the first side-portion 12, and the second side-portion 13 is perpendicular to the bottom portion 11. In addition, the first side-portion 12 may include a first flange 12, and the first flange 12 is disposed on another end (i.e. an open end) of the first side-portion 12 such that the overall first side-portion 12 forms an inverted L-shaped structure. The second side-portion 13 may include a second flange 131, and the second flange 131 is disposed on another end (i.e. an open end) of the second side-portion 13 such that the overall second side-portion 13 forms another inverted L-shaped structure which is opposite to the first side-portion 12.

The sidelight-type light source assembly 20 is disposed on the substrate 10, and the sidelight-type light source assembly 20 mainly functions to emit light to illuminate the skin. In the present invention, the sidelight-type light source assembly 20 includes a single light-emitting element 21 and a first light-guiding element 22. The light-emitting element 21 is disposed on the first side-portion 12 of the substrate 10 (i.e. the first side-portion 12 faces the sidewall of the first light-guiding element 22), and the height at which the light-emitting element 21 is placed corresponds to the height at which the first light-guiding element 22 is placed. The first flange 121 of the first side-portion 12 is located at a position above the light-emitting element 21 to assist in the effect of the light concentration and shielding for light emitted from the light-emitting element 21. Accordingly, light emitted from the light-emitting element 21 may be transmitted approximately along a lateral direction to the first light-guiding element 22 so that the first light-guiding element 22 may form a light source with a large area, e.g. the area may be greater than 5 mm*5 mm. The light-emitting element 21 may be an LED light source and the first light-guiding element 22 may be a light guide plate, for example, but the invention is not limited thereto.

In one embodiment of the present invention, the sidelight-type light source assembly 20 further includes a first dot portion 23. The first dot portion 23 is formed on a surface of the first light-guiding element 22 facing the bottom portion 11. The first dot portion 23 is mainly composed of a plurality of 3-dimensional constructions with curved surfaces. When light from the light-emitting element 21 is transmitted to any one of the 3-dimensional constructions of the first dot portion 23, the light is refracted or reflected by the 3-dimensional constructions. The refraction or reflection changes the direction of the light entering the first light-guiding element 22, thereby achieving the effect of light uniformity.

In one embodiment of the present invention, the sidelight-type light source assembly 20 further includes a light-emitting coating 24. The light-emitting coating 24 is formed on a surface of the first light-guiding element 22 opposite to the bottom portion 11, i.e. the surface facing skin. Therefore, light emitted by the sidelight-type light source assembly 20 is transmitted through the first light-guiding element 22 and thereafter necessarily through the light-emitting coating 24 to reach the skin. Since the light-emitting coating 24 is a conventional structural design used in the light guide plates, it is not described in detail herein.

The sidelight-type light sensing assembly 30 is disposed on the substrate 10, and the sidelight-type light sensing assembly 30 mainly serves to receive the light transmitted from the skin through the diffuse reflection thereon. The light-sensing element 31 is disposed on the second side-portion 13 of the substrate 10 (i.e. the second side-portion 13 faces the sidewall of the second light-guiding element 32), and the installation height of the light-sensing element 31 corresponds to the installation height of the second light-guiding element 32. The second flange 131 of the second side-portion 13 is located at a position above the light-sensing element 31 to assist in the light concentration and shielding effect for the light to be received by the light-sensing element 31. Accordingly, the second light-guiding element 32 may form a large-area light collector. The light-sensing element 31 may be a photodetector, and the second light-guiding element 32 may be a light guide plate, for example, but the invention is not limited thereto In one embodiment of the present invention, the sidelight-type light sensing assembly 30 further includes a second dot portion 33. The second dot portion 33 is formed on a surface of the second light-guiding element 32 facing the bottom portion 11. The second dot portion 33 is mainly composed of a plurality of 3-dimensional constructions with curved surfaces. When light from the outside of the module is transmitted through the second light-guiding element 32 to any one of the 3-dimensional constructions of the second dot portion 33, the 3-dimensional constructions generate the effect of light refraction or reflection, thereby changing the transmitting direction of the light and guiding the light to the light-sensing element 31.

In one embodiment of the present invention, the sidelight-type light sensing assembly 30 further includes a light-receiving coating 34, The light-receiving coating 34 is formed on a surface of the second light-guiding element 32, which faces the skin and is opposite to the bottom portion 11. Light diffusely reflected from the skin must pass through the light-receiving coating 34 prior to being transmitted to the second light-guiding element 32. Since the light-receiving coating 34 is a conventional structural design used in light guide plates, it is not described in detail herein.

The blocking member 40 is disposed between the sidelight-type light source assembly 20 and the sidelight-type light sensing assembly 30. The blocking member 40 serves to block the sidelight-type light source assembly 20 from the sidelight-type light sensing assembly 30. In one embodiment of the present invention, the blocking member 40 connects the first light-guiding element 22 and the second light-guiding element 32. The blocking member 40 may be made from an opaque material, such as black gel. Consequently, the blocking member 40 may prevent the mutual interference of light emitted from the sidelight-type light source assembly 20 and light receipted by the sidelight-type light sensing assembly 30. Furthermore, the blocking member 40 serves to fix the connection between the first light-guiding element 22 and second light-guiding element 32.

In the present invention, the sidelight-type non-invasive glucose monitoring module 1 further includes a reflective element 50. The reflective element 50 is disposed on the bottom portion 11 of the substrate 10 and is situated between the bottom portion 11 and each of the first light-guiding element 22 and the second light-guiding element 32. The reflective element 50 may reflect light emitted from the light-emitting element 21, and direct the light outward from the module through the first light-guiding element 22. Additionally, the reflective element 50 may reflect light transmitted from the outside to the light-sensing element 31 through the second light-guiding element 32. Furthermore, the reflective element 50 is positioned between the bottom portion 11 and each of the first dot portion 23 and the second dot portion 33. This allows the reflective element 50 to reflect light directly from the light-emitting element 21 or light refracted through the first dot portion 23 to the outside of the module through the first light-guiding element 22. Similarly, the reflective element 50 may also reflect light directly from the outside of the module or light refracted through the second dot portion 33 to the light-sensing element 31.

Additionally, in one embodiment of the present invention, an opaque sealing member 60 is used to connect with the junction of the sidelight-type light source assembly 20 and the substrate 10 and the junction of the sidelight-type light sensing assembly 30 and the substrate 10. The sealing member 60 may be made from the black gel, as previously mentioned. The opaque sealing member 60 prevents light leakage at the seams between different components in the module and ensures the sealing of the entire module.

In the practical operation of the sidelight-type non-invasive glucose monitoring module 1 according to the present invention, light is first emitted along a lateral direction from the single light-emitting element 21 positioned on the first side-portion 12. The emitted light can directly enter the first light-guiding element 22 or be reflected or refracted into the first light-guiding element 22 through the first dot portion 23 and/or the reflective element 50, thus causing the first light-guiding element 22 to function as a large-area light-emitting structure. Subsequently, the light travels from the first light-guiding element 22, through the light-emitting coating 24, to the skin, where it performs the necessary blood glucose sensing operation.

Subsequently, light diffusely reflected from the skin can pass through the light-receiving coating 34 and enter the second light-guiding element 32, thereby turning the second light-guiding element 32 into a large-area light-receiving structure. Then, the light can be directly laterally transmitted to the light-sensing element 31, or the light may be transmitted to the light-sensing element 31 through the processes of reflection and/or refraction associated with the second dot portion 33 and/or the reflective element 50. In the end, the single light-sensing element 31 performs subsequent operations for sensing and analyzing the blood glucose according to the received light.

As a result, the sidelight-type non-invasive glucose monitoring module 1 according to the present invention utilizes a combination of the sidelight-type light source assembly 20 and the sidelight-type light sensing assembly 30. It accomplishes blood glucose sensing with only a single light-emitting element 21 and a single light-sensing element 31, effectively reducing the number of components and manufacturing costs while achieving a thinner structure (with thickness reduced to approximately half of the conventional non-invasive blood glucose sensing modules, approximately 1 mm). Furthermore, the sidelight-type non-invasive glucose monitoring module 1 according to the present invention can adjust the dimensions of the first light-guiding element 22 and the second light-guiding element 32 to cater to different design requirements, thereby altering the area over which it can sense (e.g., suitable for large-area sensing).

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A sidelight-type non-invasive glucose monitoring module, comprising:

a substrate comprising a bottom portion;

a sidelight-type light source assembly disposed on the substrate, the sidelight-type light source assembly comprising a light-emitting element, a first light-guiding element, and a first dot portion, wherein the first dot portion is formed on a surface of the first light-guiding element and faces the bottom portion;

a sidelight-type light sensing assembly disposed on the substrate, the sidelight-type light sensing assembly comprising a light-sensing element, a second light-guiding element, and a second dot portion, wherein the second dot portion is formed on a surface of the second light-guiding element and faces the bottom portion; and a blocking member disposed between the sidelight-type light source assembly and the sidelight-type light sensing assembly to block the sidelight-type light source assembly from the sidelight-type light sensing assembly, wherein the blocking member is made from an opaque material and is connected to the first light-guiding element and the second light-guiding element, wherein the first dot portion and the second dot portion are composed of a plurality of 3-dimensional constructions with curved surfaces, and the sidelight-type light sensing assembly is configured to receive diffusely reflected light from skin to obtain blood glucose-related information.

2. The sidelight-type non-invasive glucose monitoring module according to claim 1, wherein the substrate further comprises a first side-portion and a second side-portion, the first side-portion being opposite to the second side-portion, wherein the light-emitting element is disposed on the first side-portion, and the light-sensing element is disposed on the second side-portion.

3. The sidelight-type non-invasive glucose monitoring module according to claim 2, further comprising a reflective element disposed on the substrate and between the bottom portion and each of the first light-guiding element and the second light-guiding element, the reflective element is configured to reflect a light emitted from the light-emitting element, or to reflect the light to the light-sensing element.

4. The sidelight-type non-invasive glucose monitoring module according to claim 2, wherein the sidelight-type light source assembly further comprises a light-emitting coating formed on a surface, opposite to the bottom portion, of the first light-guiding element.

5. The sidelight-type non-invasive glucose monitoring module according to claim 2, wherein the sidelight-type light sensing assembly further comprises a light-receiving coating formed on a surface, opposite to the bottom portion, of the second light-guiding element.

6. The sidelight-type non-invasive glucose monitoring module according to claim 1, further comprising an opaque sealing member connected with a junction of the sidelight-type light source assembly and the substrate and a junction of the sidelight-type light sensing assembly and the substrate.

* * * * *